US00PP19883P2

(12) United States Plant Patent
Egger

(10) Patent No.: US PP19,883 P2
(45) Date of Patent: Mar. 31, 2009

(54) ***CAMPANULA* PLANT NAMED 'BLUE-EYED BLONDE'**

(50) Latin Name: *Campanula persicifolia*
Varietal Denomination: Blue Eyed Blonde

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/150,170

(22) Filed: Apr. 25, 2008

(51) Int. Cl.
*A01H 5/00* (2006.01)

(52) U.S. Cl. ..... Plt./414

(58) Field of Classification Search ..... Plt./414
See application file for complete search history.

*Primary Examiner*—Kent L Bell
(74) *Attorney, Agent, or Firm*—Klarquist Sparkman, LLP

(57) ABSTRACT

A new and distinct *Campanula* plant characterized by yellow to yellow green foliage, large, blue bellflowers in upright and decumbent stalks, a compact, low habit, and excellent vigor.

1 Drawing Sheet

Botanical denomination: *Campanula persicifolia.*
Variety designation: 'Blue-Eyed Blonde'.

BACKGROUND OF THE INVENTION

The present invention relates to a new and distinct *Campanula* and given the cultivar name of 'Blue-Eyed Blonde'. *Campanula* is in the family Campanulaceae. The new cultivar originated from planned breeding program to produce a blue flowering, yellow leaf *Campanula persicifolia.* The original parent plant used was *Campanula persicifolia* 'Double Blue' (an unpatented plant) as the seed parent and *Campanula persicifolia* 'Kelly's Gold' (an unpatented plant) as the pollen parent. Several generations were needed to produce yellow leaf, blue-flowered offspring. 'Blue-Eyed Blonde' was selected as the best seedling for vigor, broad leaves, and large attractive blue flowers. Compared to the seed parent, *Campanula persicifolia* 'Double Blue' the new cultivar has gold rather than green leaves and single blue rather than double blue flowers. Compared to the pollen parent, *Campanula persicifolia,* 'Kelly's Gold', the new cultivar has large blue flowers rather than medium size white tinted blue flowers.

SUMMARY OF THE INVENTION

This new *Campanula* is distinguished by:

1. yellow to yellow green foliage,
2. large, blue bellflowers in decumbent and upright stalks,
3. a compact, low habit, and
4. excellent vigor.

To the inventor's knowledge, this combination of yellow foliage and blue flowers is new and unique in *Campanula persicifolia.*

This new cultivar has been reproduced only by asexual propagation (cuttings and tissue culture). Each of the progeny exhibits identical characteristics to the original plant. Asexual propagation by tissue culture using standard micropropagation techniques with terminal shoots, as done in Canby, Oreg. shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a close up of the flowers of *Campanula* 'Blue-Eyed Blonde' in May in Canby, Oreg.

FIG. 2 shows a group of 2 year old plants in summer in the garden in Canby, Oreg.

DETAILED PLANT DESCRIPTION

The following is a detailed description of the new *Campanula persicifolia* based on observations of two year old specimen grown in the trial beds outside in full sun under typical weathers in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Form.*—Rosette-forming herbaceous perennial.
- *Hardiness.*—USDA Zone 4–9.
- *Size.*—10 cm tall from the ground to the top of the foliage and 25 cm wide.
- *Habit.*—Low mound.
- *Vigor.*—Excellent.

Leaf:
- *Type.*—Simple.
- *Shape.*—Lanceolate.
- *Arrangement.*—Rosette.
- *Blade size.*—Grows to 13 cm long and 2 cm wide, usually smaller.
- *Margin.*—Crenate.
- *Apex.*—Acuminate.
- *Base.*—Attenuate.
- *Venation.*—Pinnate.
- *Surface texture.*—Glabrous on both surfaces.
- *Petiole.*—None.

*Color.*—Top and bottom sides—Yellow 13B darkening to Yellow Green 144B where shaded.

Flowering stem: leafy, sometimes decumbent, grows to 50 cm, with internodes up to 2 cm long, grows to 8 mm wide, glabrous, Yellow Green 147C.

Inflorescence:

*Type.*—Terminal raceme.

*Number of flowers per raceme.*—50 to 60.

*Pedicel.*—Grows to 2.3 cm long, 2.5 mm wide, glabrous, Yellow Green 145B.

Flower bud:

*Size.*—2.3 cm long and 1 cm wide.

*Shape.*—Ovoid.

*Color.*—Yellow Green 145C to Violet Blue 91B.

Flower:

*Type.*—Perfect, up facing.

*Size.*—3 cm deep and 6 cm to 7 cm wide.

*Shape.*—Broadly campanulate.

*Corolla description.*—3 cm deep and 6 cm to 7 cm wide, both sides Violet Blue 90C to 90D, glabrous inside and out; 5 lobes, slightly reflexed, each triangular, 14 mm long and 25 mm wide, entire, tip acute.

*Calyx description.*—23 mm wide and 8 mm deep, campanulate, 5 lobes, deeply cut, glabrous inside and out; 5 lobes, slightly reflexed, each triangular, 10 mm long and 3 mm wide, ovate, entire, tip acute, Yellow Green 146B.

*Pistil description.*—2.9 cm long, inferior ovary 5 mm deep; style 4 mm long, White 155D; 3 branched stigma, each branching again, 12 mm to 17 mm long and spreading 3 cm wide.

*Stamen description.*—10 in number, 12 mm long, filaments 2 mm to 3 mm long, Yellow White 158C, anthers 8 mm long, Yellow White 158B; pollen Yellow White 158B.

*Bloom period.*—May through June in Canby, Oreg.

*Lastingness of bloom.*—Each flower lasts about a week.

*Fragrance.*—None.

Fruit: none seen.

Seed: none seen.

Pest and, diseases: *Campanula* are troubled by snails and slugs, aphids, and spider mites. This variety has no known resistances.

I claim:

1. A new and distinct *Campanula* plant as herein illustrated and described.

* * * * *

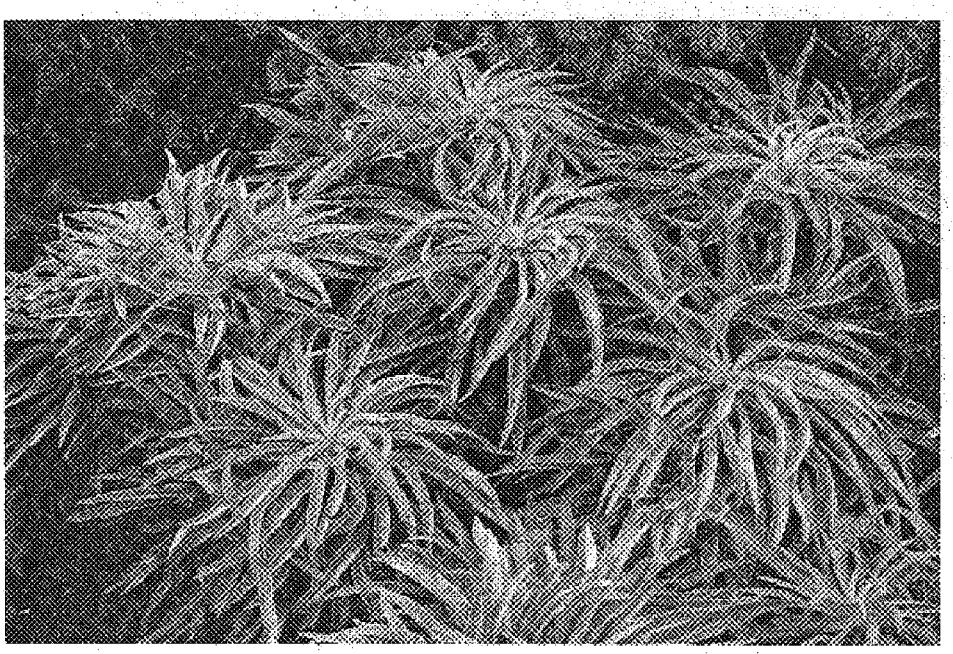

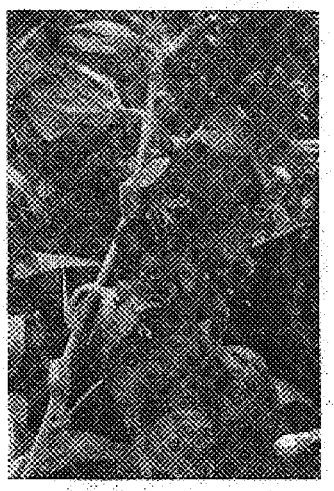
Figure 1, right
Figure 2, below